United States Patent [19]

Dailey et al.

[11] Patent Number: 4,581,121
[45] Date of Patent: Apr. 8, 1986

[54] FREE CHLORINE GAS ANALYZER

[75] Inventors: Leo L. Dailey, Philadelphia; Daniel J. Soltz, Norristown, both of Pa.

[73] Assignee: Fischer & Porter Company, Warminster, Pa.

[21] Appl. No.: 739,073

[22] Filed: May 29, 1985

[51] Int. Cl.⁴ .............................................. G01N 27/54
[52] U.S. Cl. .................................... 204/406; 204/1 T; 204/415
[58] Field of Search ...................... 204/406, 415, 1 B; 324/425

[56] References Cited

U.S. PATENT DOCUMENTS 4,441,979 4/1984 Dailey ................................ 204/402

Primary Examiner—G. L. Kaplan
Attorney, Agent, or Firm—Michael Ebert

[57] ABSTRACT

A free chlorine analyzer including a probe immersible in chlorinated water having oxygen dissolved therein, the analyzer being adapted to continuously and accurately measure the concentration of free chlorine in the water without regard to its oxygen content. The probe includes a noble metal measuring electrode, an oxidizable metal counter electrode and an electrolyte which in combination with the electrodes defines an electrochemical cell whose output current depends on the amount of the chlorine passing into the cell through a diffusion membrane permeable to this gas. The cell is connected through one or more serially-connected diodes operating in the forward direction to an output resistor across which is produced a voltage that depends on chlorine concentration. The voltage drop across the diodes impresses a potential on the cell which causes it to operate in a current limiting range and renders it insensitive to the oxygen content of the chlorinated water.

9 Claims, 5 Drawing Figures

FREE CHLORINE GAS ANALYZER

BACKGROUND OF INVENTION

1. Field of Invention

This invention relates generally to chlorine analysis, and more particularly to an analyzer which makes use of a probe immersible in chlorinated water having oxygen dissolved therein, the analyzer being adapted to continuously and accurately measure the concentration of free chlorine in the water without regard to its oxygen content.

2. Status of Art

Chlorination is widely used to purify water supplies. In practice, chlorine is introduced at a selected point in the water supply system, and flow then takes place through a region of flow which is sufficient for the chlorine to act effectively on the contaminants present in the water to produce a disinfecting action. In order to determine whether the amount of chlorine present is adequate to effect disinfection, measurements are made beyond the chlorine input point. The measurement output signal may also serve to regulate the feed of chlorine into the system to insure that the amount is adequate but not excessive.

The amount of chlorine added to the water is referred to as the "dosage," and is usually expressed as parts per million (ppm). The amount of chlorine consumed by bacteria, algae, organic compounds and some inorganic substances, such as iron or manganese, is designated as the "demand." The amount of chlorine remaining in the water at the time of measurement is referred to as the "residual." Residual is therefore determined by the demand subtracted from the dosage.

When chlorine dissolves in water, a mixture of hypochlorous and hydrochloric acids is formed. Actually, the hypochlorous acid dissociates into hydrogen and hypochlorite ions. In either the hypochlorous acid or hypochlorite ion form, chlorine is called "free chlorine residual." Free chlorine residual has a highly effective killing power toward bacteria.

Should the chlorinated water contain ammonia or certain amino (nitrogen-based) compounds, as is the case with sewage, then additional compounds, called chloramines, are formed. Chloramines occur almost instantaneously; and though several reactions are possible between hypochlorous acid and ammonia, chloramines collectively are referred to as "combined chlorine residual." This combined chlorine residual has a much lower bactericidal effect than free chlorine residual. The term "total chlorine" as used herein is the sum of free and combined chlorine.

The analysis of process water or wastewater in a treatment system for chlorine in its various forms (free, combined and total) has long presented problems. The typical continuous analyzer for this purpose requires that a sample be withdrawn from the process by a pump and delivered to the analyzer (see Morrow U.S. Pat. No. 4,129,479).

The presence of suspended solids in wastewater usually dictates a filter system to exclude these solids from the sample to be tested, and this in turn gives rise to maintenance problems.

In the 1984 Dailey U.S. Pat. No. 4,441,979, there is disclosed a chlorine analyzer including a probe immersible in chlorinated process water or wastewater for continuously and accurately measuring the concentration of the gas. The probe includes a noble metal measuring electrode, an oxidizable metal counter-electrode and an electrolyte which in combination with the electrodes defines an electrochemical cell whose output current depends on the amount of the gas passing into the cell through a diffusion membrane permeable to the gas being analyzed.

In order to simulate the effect of rapid sample flow past the membrane and thereby maintain the analytical sensitivity of the instrument, the probe is vertically supported through a flexible coupling and includes an internal motor having an unbalanced rotor secured to its shaft. Rotation of the rotor causes the probe to nutate about its vertical axis to simulate the effect of a rapid sample flow.

The difficulty with the Dailey analyzer is that dissolved oxygen in the water also permeates the membrane, so that the reading is not accurate unless some measure is taken to render the analyzer insensitive to the oxygen.

SUMMARY OF INVENTION

In view of the foregoing, the main object of this invention is to provide a chlorine analyzer for measuring the concentration of chlorine in process water or wastewater, the analyzer affording an accurate reading regardless of the amount of oxygen dissolved in the water.

More particularly, an object of this invention is to provide an analyzer of the above type which makes use of an electrochemical probe that is immersed in the water, the cell being operated in the impressed potential mode to render it insensitive to oxygen concentration.

Also an object of the invention is to provide an analyzer of the above-type in which the impressed potential is derived from semiconductor diodes connected in the forward direction in series with the cell, thereby avoiding the need for an external power supply and the concomitant need to isolate this supply from the analyzer.

Briefly stated, these objects are attained in a free chlorine analyzer including a probe immersible in chlorinated water having oxygen dissolved therein, the analyzer being adapted to continuously and accurately measure the concentration of free chlorine in the water without regard to its oxygen content. The probe includes a noble metal measuring electrode, and oxidizable metal counter electrode and an electrolyte which in combination with the electrodes defines an electrochemical cell whose output current depends on the amount of the chlorine passing into the cell through a diffusion membrane permeable to this gas. The cell is connected through one or more serially-connected diodes operating in the forward direction to an output resistor across which is produced a voltage that depends on chlorine concentration. The voltage drop across the diodes impresses a potential on the cell which causes it to operate in a current limiting range and renders it insensitive to the oxygen content of the chlorinated water.

OUTLINE OF DRAWINGS

For a better understanding of the invention as well as other objects and further features thereof, reference is made to the following detailed description to be read in conjunction with the accompanying drawings, wherein.

DESCRIPTION OF INVENTION

Figure 1:
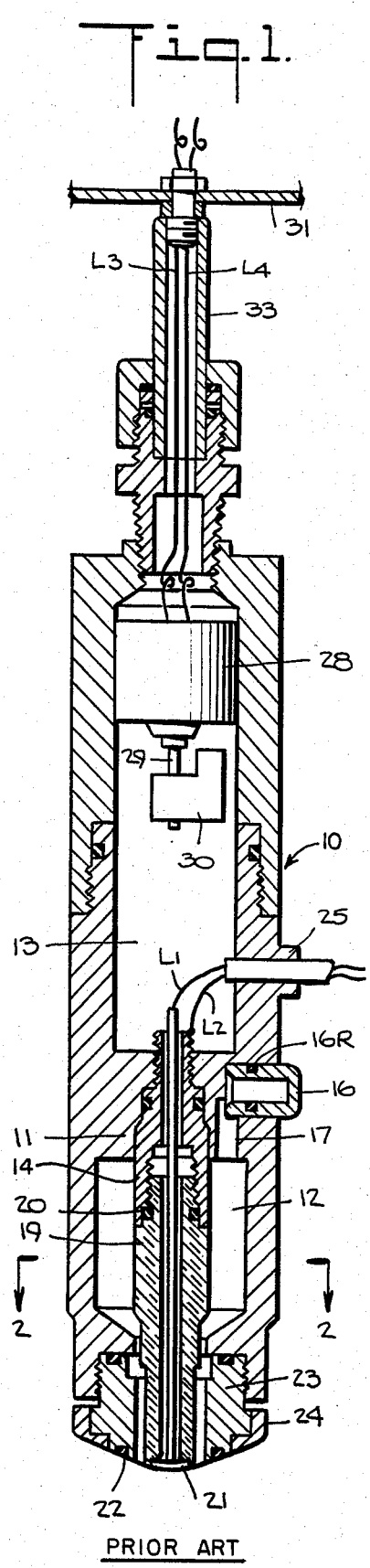
FIG. 1 is a longitudinal section taken through a membrane-type probe whose electrochemical cell is associated with an external circuit in accordance with the invention for measuring the concentration of either free or total chlorine dissolved in a stream.
Figure 2:
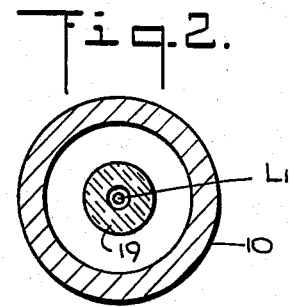
FIG. 2 is a transverse section taken in the plane indicated by line 2—2 in FIG. 1.

The Analyzer Structure:

Referring now to FIGS. 1 to 2, there is shown a membrane-type probe included in an analyzer in accordance with the invention. The probe is provided with a chlorine-responsive electrochemical cell disposed within the lower section of a hollow cylindrical casing 10. Casing 10 is fabricated of a suitable electrical insulating material having good structural strength, such as polyvinyl chloride or polycarbonate material.

Formed in casing 10 is an annular constriction 11 of reduced diameter which effectively divides the interior into a lower electrolyte chamber 12 and an upper motor chamber 13. Threadably received within constriction 11 and extending into electrolyte chamber 12 is a tubular anode 14 formed of silver. An O-ring is provided which surrounds anode 14 at its interface with constriction 11 to prevent the leakage of electrolyte from the electrolyte chamber 12 into motor chamber 13.

A fill hole in one side of the casing is sealed by a removable stopper 16. The fill hole communicates with a duct 17 leading to electrolyte chamber 12, this chamber being filled with an electrolyte appropriate to the species to be analyzed. Since stopper 16 is submerged when the probe is immersed in the liquid being tested for dissolved chlorine it is provided with an O-ring 16R to prevent leakage.

Supported coaxially within electrolyte chamber 12 is a tubular stem 19 whose upper end is socketed within the lower end of tubular anode 14 and sealed thereto by an O-ring 20. The lower end of stem 19 protrudes beyond electrolyte chamber 12, the tip of the stem having a button-shaped measuring electrode 21 mounted thereon. This measuring electrode or cathode is formed of gold or platinum.

Thus the silver anode or counter-electrode 14, the gold cathode or measuring electrode 21 and a saturated solution of an alkali bromide filling the electrolyte chamber 12 and bridging these electrodes, together define an electro chemical cell generating a current which is applied to an output resistor connected to the electrodes. The voltage developed across this resistor depends on the current flow through the cell, and, as will be explained later, this is a function of the concentration of the free chlorine being measured.

Electrolyte chamber 12 is enclosed by a semi-permeable diffusion membrane 22 which covers gold electrode 21. Membrane 22 is permeable to dissolved chlorine so that chlorine dissolved in the liquid diffuses into the electrolyte chamber. In practice, the membrane is preferably a microporous polytetrafluoroethylene material (PTFE) bonded to a polyethylene net for mechanical support. Suitable for this purpose is "Fluoropore-FG" manufactured by Millipore Corporation. This membrane has pore diameters of 0.2 micrometers ($\mu$M) and a thickness of 125 to 150 micrometers.

To stretch the membrane across the measuring electrode, its margin is clamped between an inner membrane retainer 23, threadably received within the lower end of the casing, and an outer retainer bezel 24 pressed over the inner retainer 23. Leads $L_1$ and $L_2$ from the electrodes are taken out through a port 25.

The probe assembly is vertically-mounted for immersion in the liquid being tested and has an internal motor to cause vibration or nutation of the entire probe assembly. This takes place at a rate and over an area of sufficient magnitude to produce the effect of rapid sample flow past the membrane, thereby avoiding depletion of the species being analyzed.

In nutation, the probe is caused to wobble with respect to the vertical axis, and it has the advantage over rotation about the vertical axis of minimizing the tendency to collect solids suspended in the process.

In the arrangement shown in FIG. 1, a miniature direct-current motor 28 is supported within motor chamber 11, the shaft 29 of the motor being coaxial with casing 10 so that the shaft normally lies on a vertical axis. Secured to the shaft is an eccentric or unbalanced rotor mass 30.

The probe assembly is secured to a rigid support 31 above the tank in which the probe is immersed by a flexible coupling 33 through which is extended the leads $L_3$ and $L_4$ from the motor. In practice, this coupling may take the form of a 4 or 5 inch length of ¾" I.D. flexible polyvinylchloride tubing.

As the unbalanced mass 30 is rotated by motor 28, the entire probe assembly, which is deflectable because of its flexible coupling support, is caused to nutate with respect to its vertical axis. Thus nutation takes place at a rate which is a function of motor speed and the length of the flexible coupling. As the motor speed is increased, the effective flow rate past the membrane increases, as does the probe's analytical sensitivity, in an exponential manner approaching a maximum, essentially constant condition.

The Electrochemical Operation:

When the probe is used for free chlorine analysis, the saturated solution of an alkali bromide salt (e.g. potassium bromide) is buffered to pH 4 using an acetic acid-/acetate buffer, as described in greater detail in U.S. Pat. No. 3,413,199.

Free chlorine, which diffuses through membrane 22 and enters the interior of the cell, reacts with this electrolyte to produce the bromine analog of chlorine concentration. The bromine solution is electrochemically reduced at the gold measuring electrode, generating an electrical current flow in the output resistor 18 in the external circuit shown in FIG. 3. This current is proportional to bromine concentration and therefore to chlorine concentration in the process. At the same time, the silver counter-electrode 14 is oxidized, producing silver ions which are soluble in the highly concentrated bromine electrolytic solution.

Figure 3:
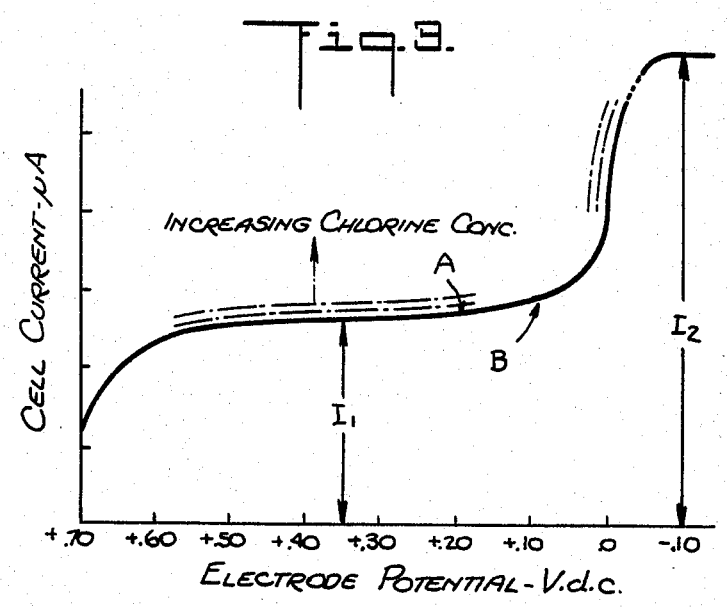
FIG. 3 is a curve showing the relationship between the potential in the electrode of the cell and the cell current.

FIG. 3 is a curve showing the current vs. electrode potential for the electrochemical cell of the probe, the current in terms of microamperes being plotted against electrode potential on a scale from −0.10 Vdc to +0.70 volts.

In the curve, the current $I_1$ is that due to electrochemical reduction of chlorine (bromine analog), while the current $I_2$ is that due to the reduction of chlorine plus oxygen. Point A in the curve is the potential at which oxygen reduction begins, and point B in the curve is the galvanic potential of the cell with substantially no bias voltage thereon.

In the galvanic mode, the cell electrode assumes potential B, where it will be seen that the output current $I_2$ is affected by both chlorine and oxygen; hence the probe in this mode is also sensitive to oxygen concentration and does not provide an accurate reading of chlorine concentration. Any small change in galvanic potential or in oxygen concentration will result in a shift in output current $I_2$ and will appear as an error.

Over the bias potential range of about +0.6 to +0.3 volts dc, the cell current $I_1$ is relatively constant and is responsive only to electrochemical reduction of the bromine analog of chlorine. As the chlorine level increases with an accompanying increase in current flow, the galvanic potential moves toward zero to increase the oxygen error. Increased oxygen concentration moves the oxygen error in the positive direction, thereby reducing the range over which oxygen error is negligible.

Figure 4:
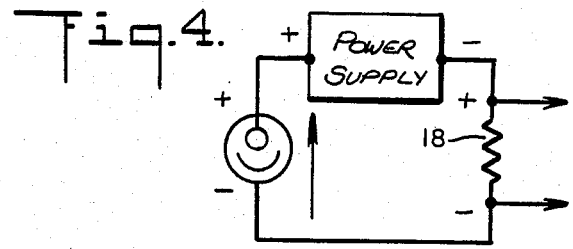
FIG. 4 is a schematic diagram of the probe circuit using an external power source for the impressed potential.

The External Circuit:

As shown in FIG. 4, the electrochemical cell formed by anode 14 and measuring electrode or cathode 21 is connected to load resistor 18 through a d-c power supply 33 to impress a bias potential on the cell which causes it to operate in a current limiting range in which the cell is insensitive to the oxygen content of the water in which the probe is immersed.

The specific value of the impressed biased potential depends on the type of electrode material used. In practice, it has been found that a bias of 0.4 volts dc is acceptable for a cell formed of platinum and silver electrodes. However, it is not essential that the impressed potential be maintained at a constant level, for the cell will operate in the current limiting range when the bias is between about 0.3 volts to 0.6 volts.

The difficulty with using a power supply 33 in conjunction with the probe is that it not only adds to the cost of the external circuit, but it also becomes necessary to isolate the power supply so that it introduces no extraneous signals into the circuit.

Figure 5:
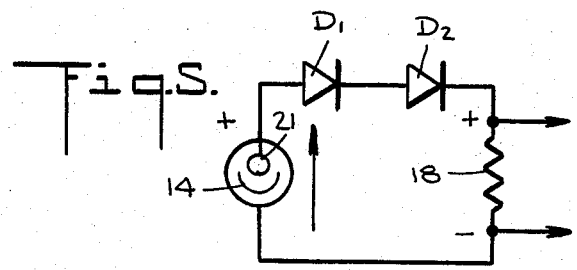
FIG. 5 is the diagram of the probe circuit using diodes for the impressed potential.

In accordance with the invention, instead of using a power supply, the impressed potential is obtainable from a pair of Schottky barrier diodes $D_1$ and $D_2$ connected in series with the cell in the forward direction, as shown in FIG. 5.

A Schottky diode is formed by contact between a semiconductor layer and a metal coating and has a non-linear rectifying characteristic. When a forward bias is applied to the interface of the metal anode and semiconductor cathode which exceeds a minimum cutoff level, current flows freely through the diode. Schottky diodes are characterized by a small forward voltage drop. For a typical forward current of 10 $\mu$A, the voltage drop is about 0.25 V for a Schottky diode and about 0.55 V for a comparable silicon pn junction diode which can be used when higher voltage drops are needed.

In order, therefore, to obtain an impressed potential of about 0.4 volts, two Schottky diodes $D_1$ and $D_2$ are connected in series to double the voltage drop thereacross. These diodes operate close to cutoff in the microampere range.

Thus, the Schottky diodes function to maintain a stable low voltage in accordance with the micro-current supplied thereto by the electrochemical probe. Because this arrangement requires no external power and requires no isolation, it is less expensive and more reliable than that shown in FIG. 3.

While there has been shown and described a preferred embodiment of a free chlorine gas analyzer in accordance with the invention, it will be appreciated that many changes and modifications may be made therein without, however, departing from the essential spirit thereof.

We claim:

1. A chlorine gas analyzer comprising:
    A. a probe immersible in chlorinated water having chlorine as well as oxygen dissolved therein, said probe including a chamber having a port covered by a diffusing membrane permeable to dissolved chlorine and oxygen, an oxidizing metal counter electrode and a noble metal measuring electrode disposed in said chamber and an electrolyte filling said chamber to bridge said electrodes to form an electrochemical cell generating a microampere current which is a function of the dissolved gas diffusing through said membrane; and
    B. an external circuit coupled to said cell, said circuit including a load resistor connected in series with at least one diode to said electrodes, the diode being connected in the forward direction with respect to the current generated by said cell to produce a voltage drop thereacross which biases the cell to operate in its current limiting range in which the cell is substantially insensitive to dissolved oxygen whereby the voltage developed across the load resistor is proportional to the chlorine content of the water.

2. An analyzer as set forth in claim 1 in which the diode is a Schottky diode.

3. An analyzer as set forth in claim 2, wherein said circuit includes a pair of Schottky diodes connected in series to produce a bias of about 0.4 volts.

4. An analyzer as set forth in claim 1, wherein said diode is a silicon pn junction diode.

5. An analyzer as set forth in claim 1, wherein said noble metal is platinum.

6. An analyzer as set forth in claim 1, wherein said oxidizable metal is silver.

7. An analyzer as set forth in claim 1, wherein said electrolyte is a saturated solution of potassium bromide buffered to pH 4.

8. A probe as set forth in claim 1, wherein said membrane is of PTFE material.

9. A probe as set forth in claim 1, further including means to nutate the probe in said water.

* * * * *